US008645343B2

(12) United States Patent
Wong et al.

(10) Patent No.: US 8,645,343 B2
(45) Date of Patent: Feb. 4, 2014

(54) PROCESSING DATA FROM GENOTYPING CHIPS

(75) Inventors: Alexander Wong, Palo Alto, CA (US); Oleksiy Khomenko, Stanford, CA (US); Serge Saxonov, Seattle, WA (US); Brian Thomas Naughton, Mountain View, CA (US); Lawrence Hon, Millbrae, CA (US)

(73) Assignee: 23andMe, Inc., Mountain View, CA (US)

( * ) Notice: Subject to any disclaimer, the term of this patent is extended or adjusted under 35 U.S.C. 154(b) by 455 days.

(21) Appl. No.: 12/583,842

(22) Filed: Aug. 25, 2009

(65) Prior Publication Data
US 2010/0057807 A1      Mar. 4, 2010

Related U.S. Application Data

(60) Provisional application No. 61/199,602, filed on Nov. 17, 2008, provisional application No. 61/190,144, filed on Aug. 26, 2008, provisional application No. 61/200,840, filed on Dec. 3, 2008.

(51) Int. Cl.
*G06F 7/00*      (2006.01)
*G06F 17/30*      (2006.01)

(52) U.S. Cl.
USPC ............. 707/700; 707/737; 707/758; 702/20

(58) Field of Classification Search
USPC ........... 707/705, 741, 700, 737, 758; 702/19, 702/20
See application file for complete search history.

(56) References Cited

U.S. PATENT DOCUMENTS

| | | | |
|---|---|---|---|
| 7,729,865 B2 | 6/2010 | Hoffman et al. | |
| 2003/0171878 A1 | 9/2003 | Frudakis | |
| 2003/0190649 A1 | 10/2003 | Aerts et al. | |
| 2004/0171051 A1* | 9/2004 | Holloway | ........................ 435/6 |
| 2009/0254588 A1* | 10/2009 | Li | ................................ 707/201 |

FOREIGN PATENT DOCUMENTS

| WO | WO 2004/061616 A2 | 7/2004 |
|---|---|---|
| WO | WO 2008/079374 A2 | 7/2008 |
| WO | WO 2008079374 A2 * | 7/2008 |

* cited by examiner

*Primary Examiner* — Vincent F Boccio
(74) *Attorney, Agent, or Firm* — Van Pelt, Yi & James LLP

(57) ABSTRACT

Processing genetic data is disclosed, including: receiving two or more genetic data sets for an individual from one or more genetic data sources; merging the genetic data sets from the one or more genetic data sources, including identifying a duplicate SNP between the genetic data sets and determining one or more data values to be stored for the duplicate SNP; and storing a single set of merged genetic data for the individual.

20 Claims, 10 Drawing Sheets

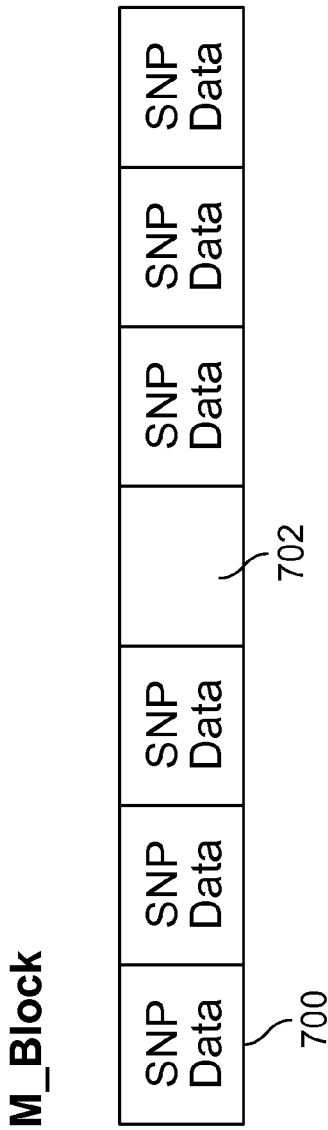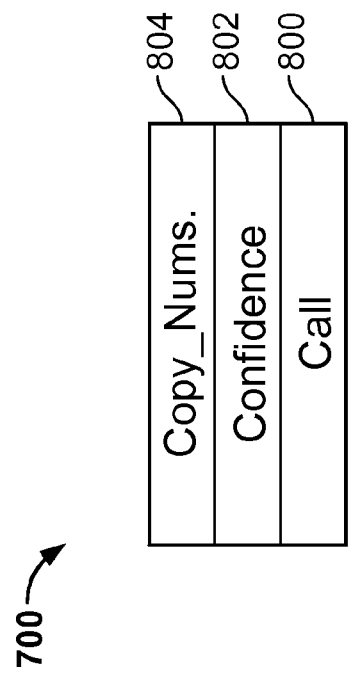

PROCESSING DATA FROM GENOTYPING CHIPS

CROSS REFERENCE TO OTHER APPLICATIONS

This application claims priority to U.S. Provisional Patent Application No. 61/199,602 entitled PROCESSING DATA FROM GENOTYPING CHIPS filed Nov. 17, 2008, U.S. Provisional Patent Application No. 61/190,144 entitled EMPIRICAL METHODS TO IMPROVE GENOTYPE CALLING filed Aug. 26, 2008 and U.S. Provisional Patent Application No. 61/200,840 entitled CUSTOM GENOTYPING CHIP filed Dec. 3, 2008 which are incorporated herein by reference for all purposes.

BACKGROUND OF THE INVENTION

The instructions for making the cells in the human body are encoded in deoxyribonucleic acid (DNA). DNA is a long, ladder-shaped molecule, in which each corresponding rung is made up of a pair of interlocking units, called bases, that are designated by the four letters in the DNA alphabet—A, T, G and C. 'A' always pairs or "bonds" with 'T', and 'G' always pairs or "bonds" with 'C'. The sequence of these four letters that make up an individual's DNA is referred to as the individual's genome.

BRIEF DESCRIPTION OF THE DRAWINGS

Various embodiments of the invention are disclosed in the following detailed description and the accompanying drawings.

FIGS. 7 and 8 are diagrams illustrating an example of a data structure or M_Block for storing the merged data sets.

DETAILED DESCRIPTION

Figure 1:
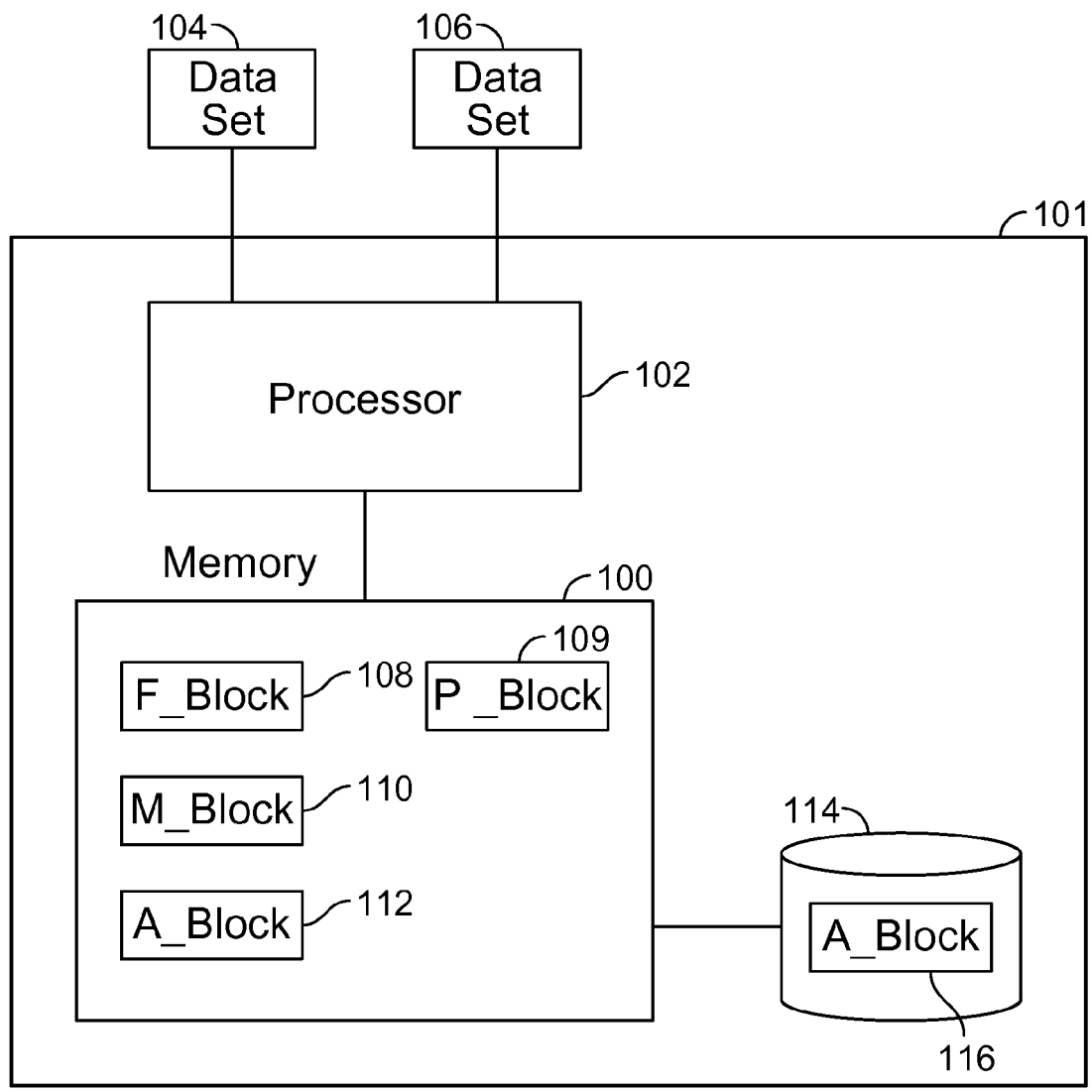
FIG. 1 is a block diagram illustrating an embodiment of a system for processing data from genotyping platforms.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

The long molecules of DNA in cells are organized into pieces called chromosomes. Humans have 23 pairs of chromosomes. Other organisms have different numbers of pairs—for example, chimpanzees have 24 pairs. Chromosomes are further organized into short segments of DNA called genes. The different letters A, T, G, and C, which make up a gene dictates how cells function and what traits to express by dictating what proteins the cells will make. Proteins do much of the work in the body's cells. Some proteins give cells their shape and structure. Others help cells carry out biological processes like digesting food or carrying oxygen in the blood. Using different combinations of the As, Cs, Ts and Gs, DNA creates the different proteins and regulates when and how they are turned on. Information about an individual's DNA sequence, including his or her genome or particular regions of the genome is referred to as genotypic information. Regions of a particular individual's genome can also be referred to as "DNA sequences."

Genotyping data includes single nucleotide polymorphisms ("SNPs"), which are the variations in the DNA sequence that occur at particular locations in an individual's DNA sequence. SNPs can generate biological variation between people by causing differences in the genetic recipes for proteins Each person has the same set of genes—about 20,000 in all. The differences between people come from slight variations in these genes. For example, it's not that a person with red hair has the "red hair gene" while a person with brown hair has the "brown hair gene." Rather, all people have genes for hair color, and different versions of these genes, i.e. differences in the regions of the genome containing the gene, dictate whether someone will be a redhead or a brunette.

Different variants of each SNP are called alleles. Those differences can in turn influence a variety of traits such as appearance, disease susceptibility or response to drugs.

While some SNPs lead to differences in health or physical appearance, some SNPs seem to lead to no observable differences between people at all. Data for each SNP contains two allele values, one inherited from the mother and one from the father.

If one were to compare the DNA of any two people, more than 99% of it is expected to be the same across any appreciable stretch of sequence. However, the less than 1% of the DNA that differs between individuals can add up to many base pairs which contain useful information about the individuals. One can imagine a spectrum; where on one end we have two unrelated people from different ethnic groups. Their DNA will differ a great deal. On the other end of the spectrum we can imagine a pair of very close relatives like a parent and a child or two siblings. When DNA is passed from parent to child it is copied almost exactly. Consequently, virtually one half of the child's DNA will be identical to that of each parent. Similarly, for a pair of siblings, virtually 50% of their DNA should be identical.

Because of recombination of DNA sequences and the independent assortment of chromosomes, the DNA of two parents is shuffled at every generation. That, in addition to the small trickle of new mutations, means that only relatives will carry long genome regions where their DNA is completely or almost completely identical. In order to determine whether a region is identical, one could sequence assay every single base pair directly or assay a large number of markers that vary between individuals. Markers are points along the genome where individuals may differ. These markers could be, but are not limited to, SNPs. A long stretch of sequence where every marker is the same between two chromosomes indicates that the rest of the sequence, which is not being assayed directly, is also identical.

Every region of a person's autosomal (restricted to "non-sex" chromosomes) genome is represented by a pair of DNA sequences, one inherited from the mother and one from the father. Therefore, for every person, every marker along the genome (including SNPs) comprises two values where one value is the variant inherited from the mother and one value is the variant inherited from the father. A child inherits virtually 50% of his or her DNA from the father and virtually 50% from the mother. The DNA inherited from the mother can be either inherited from the maternal grandmother or the maternal grandfather. The DNA inherited from the father can be inherited from the paternal grandfather or the paternal grandmother.

By submitting samples of their DNA, individuals can be provided with information associated with their DNA. In order for this information to be ascertained, individuals may provide a sample of saliva on a swab to a lab. The lab then analyzes the sample using a genotyping platform, which is a set of SNPs and a method for assaying the allele values for those SNPs. This process is known as hybridization and yields different hybridization intensity values for each allele. The lab assigns genotype values to the alleles of each SNP by comparing the relative strength of these intensities. Assigning these values to the individual's SNPs is referred to as "calling" or "genotype calling." Examples of different genotyping platforms include the Illumina HumanHap550v3 genotyping chip or full sequencing using ABI SOLiD. It would be useful to have methods that would use additional information to improve on the genotype call assigned by the hybridization process.

Individuals may submit DNA samples to a lab in order to learn specific information about their DNA. For example, an individual could submit a sample to be tested for his or her likelihood of developing type 2 diabetes. If the lab knows the type of DNA information in which the individual is interested, the lab identifies only the genotyping data or SNPs that are relevant to the information the individual seeks and uses a platform with the genotyping data necessary to determine that information. The genotyping data from the platform can then be provided to a system that analyzes individuals' DNA to provide the information the individual is seeking.

If an individual would like to have additional information about their DNA, the individual may need to submit another sample to the lab. The lab then uses another platform and another set of genotyping data can be submitted to a system that analyzes individuals' DNA to provide the information the individual is seeking. Thus, a method of processing multiple sets of genotyping data would be useful.

Processing Genotype Data

FIG. 1 is a block diagram illustrating an embodiment of a system for processing data from genotyping platforms. In the example shown, system 101 receives a data set from each of two genotyping platforms. For example, system 101 can receive the data sets from a lab over a Secure File Transfer Protocol ("SFTP") secure connection. Once system 101 has received a set of data 104 for an individual, the system processes the data set 104 using processor 102 and stores the data in a data structure in memory 100 which is coupled to processor 102. The data structure for each data set is referred to as P_Block, 108 and 109. In some embodiments, system 101 creates a P_Block 108 for each data set of genotyping information it receives. In some embodiments, when the system 101 has received more than one data set, e.g., data sets 104 and 106, for an individual, the system 101 processes the P_Blocks 108 and 109 for that individual in processor 102 and merges the data from P_Blocks 108 and 109 into a second data structure, M_Block 110, which is also stored in memory 100 coupled to processor 102. When system 101 has received only one data set for an individual, the M_Block is still created from the P_Block. M_Block 110, for example, may contain a subset of the data contained in P_Blocks 108 and 109. If there is duplicate or conflicting data in P_Blocks 108 and 109, that data is resolved, as more fully described below. In some embodiments, the processor 102 processes the data in M_Block 110 and creates a new data structure, A_Block 112, which is stored in memory 100. A_Block 112, for example, may contain only the genotyping information that is relevant to application(s) that an individual can access via a particular website. In some embodiments, a copy of A_Block 116 is stored in database 114 so that the application(s) using it can access it.

Although the example of FIG. 1 shows two data sets each received from a different genetic data source in other embodiments, any number of data sets may be received from the same or different genetic data sources, which may include data produced by different genotyping platforms.

Figure 2:
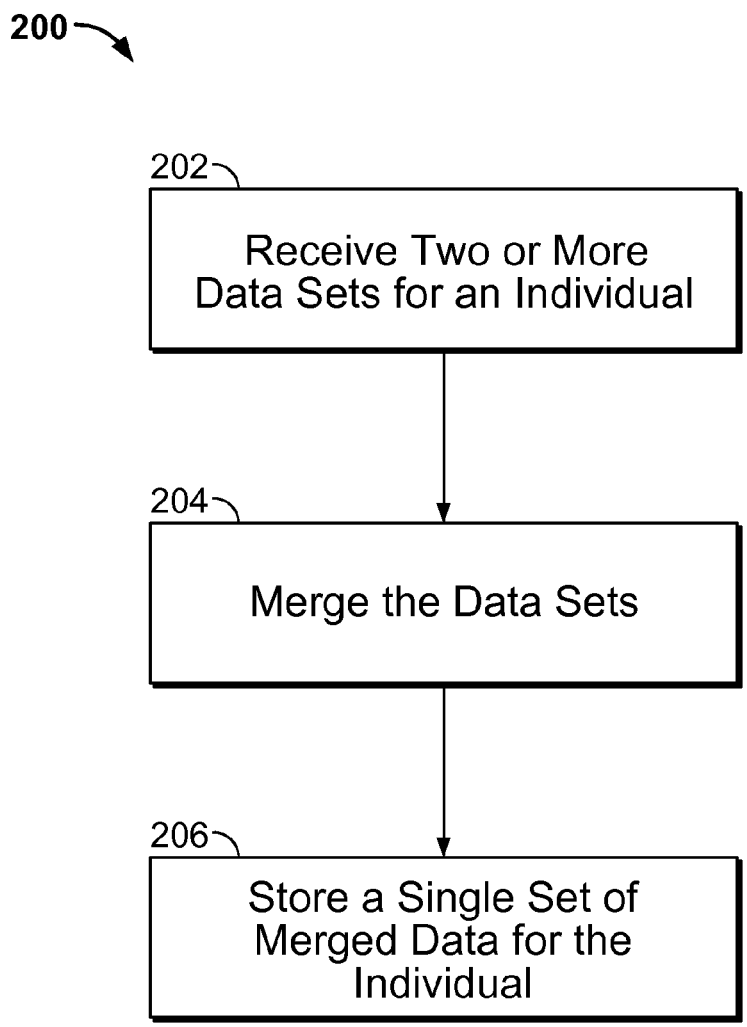
FIG. 2 is a flow chart illustrating an embodiment of a process 200 for processing data from genotyping chips.

FIG. 2 is a flow chart illustrating an embodiment of a process 200 for processing data from genotyping chips. At 202, two or more data sets of genotyping data for an individual are received. At 204, the two or more data sets for an individual are merged to create a single data set. At 206, the single set of merged data for the individual is stored. In some embodiments, the single set of merged data does not include duplicate SNP data. If data (such as a call or an intensity value) is stored for a particular SNP in the first data set and the same data is stored for the same SNP in the second data set, then the single set of merged data does not include the same data twice. For example, if the data is a call, then the single set of merged data includes only one call. This means that when merging the two or more data sets at 204, discrepancies between data for a particular SNP may need to be resolved.

For example, if the first data set includes a call of "CC" for a particular SNP and a second data set includes a call of "CT" for the same SNP, then either "CC" or "CT" might be selected to be stored for the SNP call in the single set of merged data. In some cases, "NC" (no call) or some other value (e.g., derived from the first data set and the second data set) may be stored for the SNP call in the single set of merged data.

Figure 3:
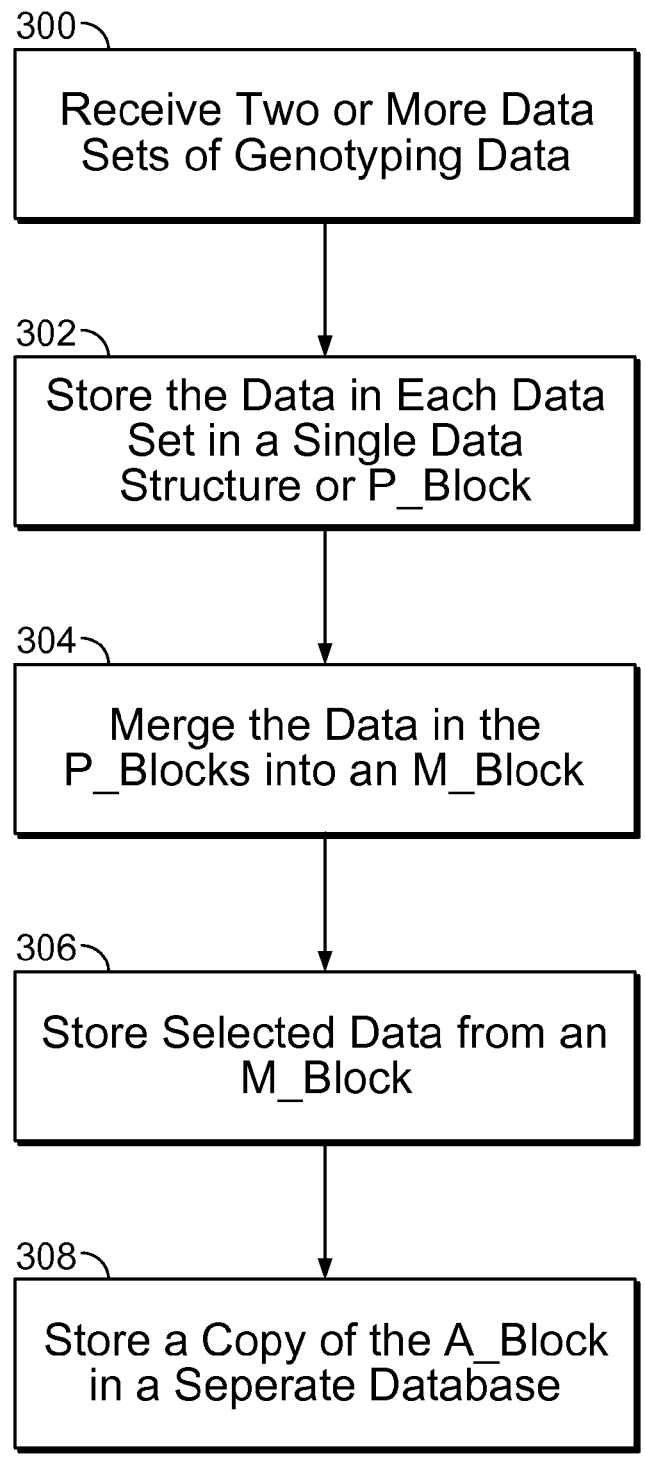
FIG. 3 is a flow chart illustrating an example of the process of FIG. 2.

FIG. 3 is a flow chart illustrating an example of the process of FIG. 2. At 300, two or more data sets of genotyping data for an individual are received from two or more genotyping platforms. At 302, data in each data set is stored in memory.

An example of storing the data sets in memory is illustrated by the system shown in FIG. 1. Once a data set 104 or 106 of genotyping information is received by the system 101, the processor 102 processes the information and stores it in a data structure. An example of a data structure for storing a data set 104 or 106 is P_Block 108 or 109. A P_Block is shown in more detail in FIG. 5.

Figure 5:
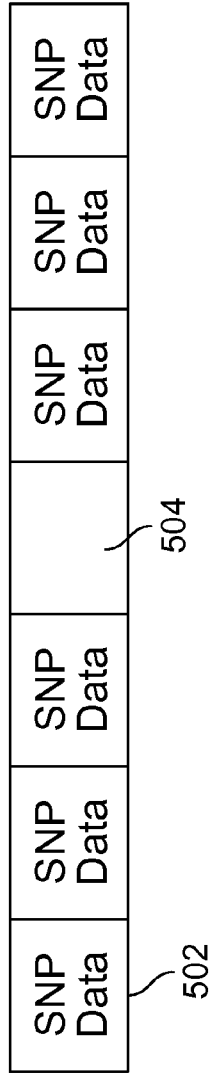
FIG. 5 is a diagram illustrating an example of a data structure or P_Block for storing the data in each data set.
Figure 6:
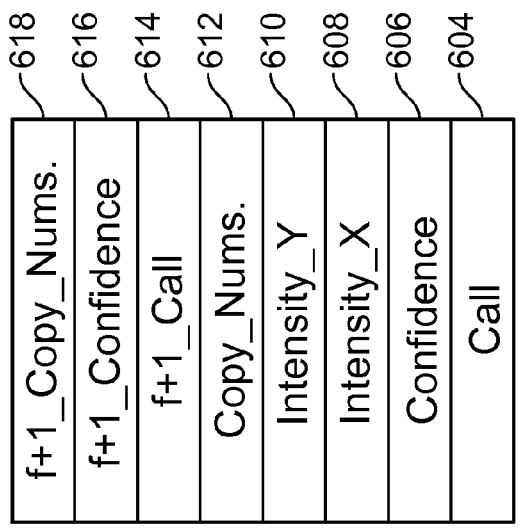
FIG. 6 is a diagram illustrating an example of the fields that may be included in an entry of a P_Block.

FIG. 5 is a diagram illustrating an example of a data structure or P_Block for storing the data in each data set. In this example, P_Block 108 contains an entry 502 for each SNP in the genotyping data set that has been received. FIG. 6 is a diagram illustrating an example of the fields that may be included in an entry of a P_Block. In some embodiments, entry 502 of the P_Block includes the following fields: the particular genotype of the SNP or call 604; the confidence level of the call or confidence 606; the probe illumination intensity x or intensity_x 608; the probe illumination intensity y or intensity_y; the estimated number of copies of the alleles found in the individual's DNA or copy_nums 612; the call made by the lab or ftl_call 614; the confidence level determined by the lab or ftl_confidence 616; and the lab's estimated number of copies or ftl_copy_num 618. In some embodiments, the P_Block's entries only include the information received from the lab from the chip.

An example of a specification for an entry in the P_Block is shown below:

```
{
    call            // genotype call e.g. 'AG'
    confidence      // confidence level of the call
    intensity_x     // probe illumination intensity X
    intensity_y     // probe illumination intensity Y
    copy_nums       // estimated number of copies
            // members for preserving calls as they came
            from the lab
            // in case we re-call ourselves and overwrite
            the fields above.
            // FTL stands for "from the lab"
    ftl_call        // genotype call
    ftl_confidence  // lab's confidence level of the call
    ftl_copy_nums   // estimated number of copies
}
```

Figure 4:
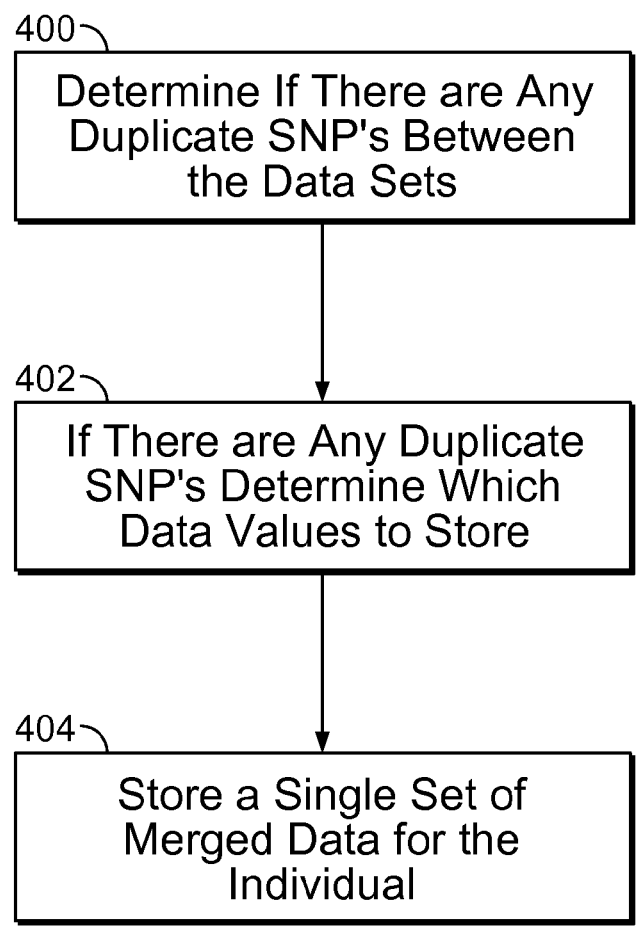
FIG. 4 is a flow chart illustrating an embodiment of merging the data from all the P_blocks for an individual and storing that individual's data in an M_Block.

Returning to FIG. 3, at 304, the system merges the data from all of the P_Blocks for an individual into a single set of data and stores the data in a single data structure, such as an M_Block. FIG. 4 is a flow chart illustrating an embodiment of merging the data from all the P_blocks for an individual and storing that individual's data in an M_Block. In some embodiments, this process is used to perform step 304. At 400 data in the plurality of P_Blocks for a particular individual is analyzed to determine if there are any duplicate SNPs. There are duplicate SNPs if there are SNPs that are included in more than one P_Block or if any P_Block contains duplicate SNPs. If there are any duplicate SNPs for an individual, then at 402, the data for each of these SNPs is analyzed to determine which data values will be stored in the M_Block. In various embodiments, a variety of techniques may be used to analyze the data. Merging an individual's data into one data set allows the system to run more efficiently when analyzing and presenting the individuals DNA data.

In some embodiments, determining which data values will be stored in the M_Block for a particular SNP with duplicates includes iterating through the list of probes associated with the SNP. The probe ranked first in the list is examined first, and if the P_block entry for the probe contains a call, that call is stored in the M_block. If the P_block entry for the first probe is a no-call, then the second ranked probe is examined. If the second probe contains a call, then that call is stored in the M_block. Otherwise the iteration continues until a call is found or no more probes associated with the SNP are left. If no probe associated with the SNP contains a call in any of the P_blocks, a "no-call" is stored in the M_block. In some embodiments consensus calls would first be established for each P_block by iterating over all the probes associated with the SNP within the P_block. If every P_block yields the same consensus call for the SNP then that call is stored in the M_block. If the calls disagree, the call stored in the M_block could be a "no-call" or could be based on a majority vote among the consensus calls from all the P_blocks. In some embodiments other methods can be used for combining calls for the same SNP from multiple platforms. For example, one platform could have higher precedence and would override calls from other platforms. Also, one can incorporate confidence or likelihood scores associated with the calls from individual P_blocks, to determine the most likely call to store in the M_block. In some embodiments the determination of the call to be stored in the M_block can make use of other data in addition to or instead of calls stored in P_blocks.

In some embodiments calls to be stored in the M_block for a particular SNP can be derived from intensity values in P_block entries for probes associated with the SNP. One way to derive calls from intensity values in one or multiple probes is by computing average intensities across the probes. For example, if a SNP has two alleles A and G, each probe may have one intensity value associated with A and another intensity value associated with G. One can use average intensity values for each of the two alleles to determine the call to store in the M_block. For example, high average intensity for A would indicate that the call should be AA, while high average intensity for G would indicate that the call should be GG. Intermediate intensities for both alleles would suggest that the call should be AG. When both intensities are too low or too high the call could be set to a "no-call". Establishing which combinations of intensity values (averaged or not) correspond to which calls can be done using a variety of techniques including various machine learning approaches (such as Gaussian mixture models or Support Vector Machines) or empirical heuristics. Some embodiments can take additional information into account when determining calls. This information can include data from nearby SNPs, linkage disequilibrium (LD) estimates, family information, and population specific information. More detail about each of these methods is discussed below.

At 404 the data for an individual is then stored as a single set of merged data for the individual in a data structure, such as M_Block 110 shown in FIG. 1. FIGS. 7 and 8 are diagrams illustrating an example of a data structure or M_Block for storing the merged data sets. The M_Block in FIG. 7 includes one entry 700 for each SNP for which data has been received for an individual. The order and/or location of the SNPs in the M_Block are set so that they are the same for every individual and so that the entire M_Block represents a union of unique SNPs that are found on any one of the supported genotyping platforms. When support for a new platform is added to the system, any SNPs that exist on that platform, but not on any previously supported platform, are added to the end of the existing M_Block layout. This way, the location of the entry exactly determines what SNP is represented by the entry. For example, in FIG. 8, each entry (or slot) in the M_block corresponds to a particular SNP. In these embodiments, if no data has been received for a particular SNP, there will be a blank entry 702 at the location in the M_Block for that SNP's data. Also, in these embodiments, a lookup table or a configuration file can be used to map the position of the SNPs in the M_Block to their descriptions and locations on the chromosome positional index in the human genome and vice versa. By storing information for all of an individual's SNPs in one data structure, an application using the data is able to access efficiently the genotyping information about the individual, as more fully described below.

If all M_Blocks are laid out identically as described above, an application only needs to access a single fixed-size index (lookup table, configuration file) to map SNPs to M_Block positions and vice versa regardless of how many genotypes are in the system. Any computation that depends on a fixed subset of SNPs (e.g. risk, ancestry) can be performed for any number of genotypes by looking up the positions of required SNPs only once, and then accessing the same fixed positions in different M_Blocks over and over again. An application can also perform any computation that depends on all SNPs (e.g. similarity) by looking at the data in two or more M_Blocks in position order because by construction the data in the same position represents the same SNPs.

When support for a new genotyping platform is added to the system, it is possible that in some embodiments some genotypes will be stored in longer M_Block than other genotypes that were previously loaded into the system. In that case the application can treat the shorter M_Block as if it is padded with blank values.

In some embodiments, an entry 700 of the M_Block includes the following fields: the genotype call or call 800; the confidence level of the call or confidence 802; and the estimated number of copies or copy_nums 804.

An example of a specification for an entry in the M_Block is shown below:

```
{
    call          // genotype call
    confidence    // confidence level of the call
    copy_nums     // estimated number of copies
}
```

In some embodiments, if an M_Block already exists for an individual and the system receives an additional data set of genotyping information for the individual, the system can create a new P_Block for the new information in the manner discussed above and then merge the existing M_Block with the new P_Block in a similar manner.

Figure 9:
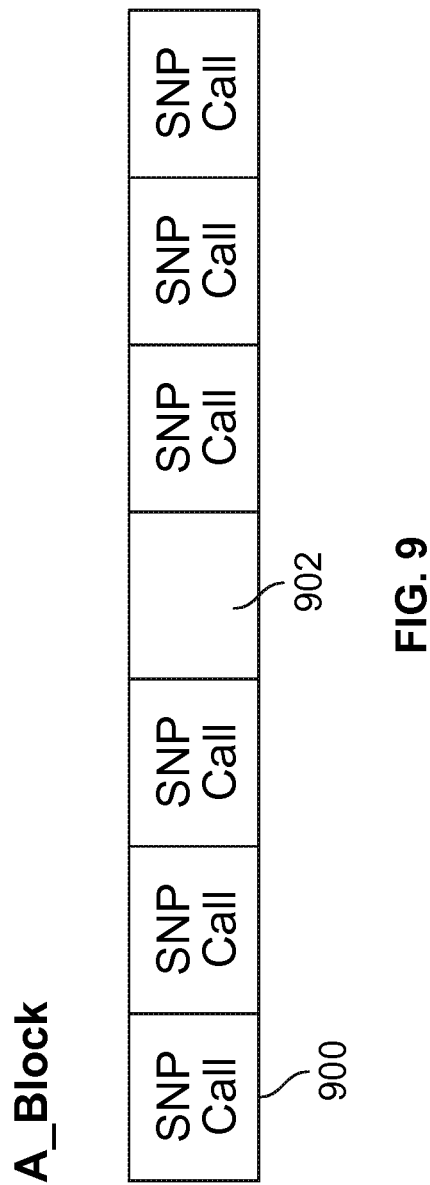
FIG. 9 is a diagram illustrating an example of a data structure or A_Block for storing the merged data.

Returning to FIG. 3, at 306, in some embodiments data is selected from the M_Block and is stored in another data structure, A_Block 112 shown in FIG. 1. In some embodiments, the data in A_Block 112 is a subset of the data in the M_Block. In some embodiments, the data in A_Block 112 is derived from the data in the M_Block. FIG. 9 is a diagram illustrating an example of a data structure or A_Block for storing the merged data. Multiple types of A_Blocks can co-exist in the system for different purposes. All A_Blocks are derived from M_Blocks and serve the purpose of optimizing application's access to genotype data by presenting smaller subsets of data appropriate for different needs. The order and/or location of the SNPs in each type of A_Block are set so that they are the same for each individual. If no data has been received for a particular SNP, there will be a blank entry 902 at the location in the A_Block for that SNP's data. A_Blocks enjoy the same indexing and performance benefits as were previously described for M_Blocks.

In some embodiments, an entry 900 in an A_Block includes the genotype call for each SNP.

An example of a specification for an entry in the A_Block is shown below:

```
{
    call    // genotype call
}
```

At 308 of FIG. 3, a copy of the A_Block is stored in a separate database. Thus, calls for all individuals' SNPs that the system is aware of can be accessed from one data structure. This single data structure allows for greater efficiency by an application accessing the individual's genotyping information for analysis and presentation.

In some embodiments, step 306 is skipped and A_Blocks are not generated. For example, M_Blocks may be accessed and used by an application.

In some embodiments, the database containing the A_Blocks can be a database connected to a website that allows individuals to learn more about the DNA. An example of such a website is www.23andme.com. An individual may use such a website to ascertain descriptions of certain traits they have and the genes associated with them. For example, the website www.23andme.com provides an odds calculator that can combine genetic information, age, and ethnicity to get an idea of which common health concerns are most likely to affect the individual. Such an odds calculator may be used by an individual to determine information for an individual such as his or her likelihood of developing Type 2 diabetes. Additionally, such a website may allow an individual to determine if they have a particular gene variant, such as the one that allows for tasting the bitter flavor of broccoli. The website may also allow comparison operations between individuals' genomes. For example, the website may be able to determine if two individuals are related or ascertain an individual's ethnicity make-up.

Having all of the calls for all of an individual's SNPs located in one data structure, such as an A_Block, in the database used by the website, allows the system to access efficiently the data needed to analyze the individual's DNA. This efficiency allows the website to provide the information to the individual more quickly. Additionally, the consistency of the layout of the single data structure, such as an A_BLOCK, allows for efficient comparisons of genomes even if the data are derived from multiple platforms. Because there is one data structure containing all of the individual's SNPs calls, the system does not have to access different data sets, such as P_Blocks, for the individual in order to determine which SNPs are in a particular data set or to determine which call to use if there is more than one call for a SNP in individual's data sets. Avoiding this process allows the system to work more efficiently and provide the individual with the results of their DNA analysis more quickly.

Genotype Calling

As explained above, data for each SNP contains two allele values, one inherited from the mother and one from the father. When individuals submit samples of their DNA to a lab, the lab may analyze the sample using a genotyping platform, which may include complementary sequences of DNA in which the values of the bases are known. This process is known as hybridization and yields hybridization intensity values for each allele of a SNP, a two-dimensional vector of "intensities." Hybridization is based on the fact that nucleotides will bind to their complements, creating a strong bond, referred to as annealing. The intensity value is a measure of the strength of this bond. In some embodiments, genotype calling refers to making a call for a specific SNP. In some embodiments, genotype calling refers to determining a sequence of genotype calls for an individual (i.e., DNA sequencing).

Figure 10A:
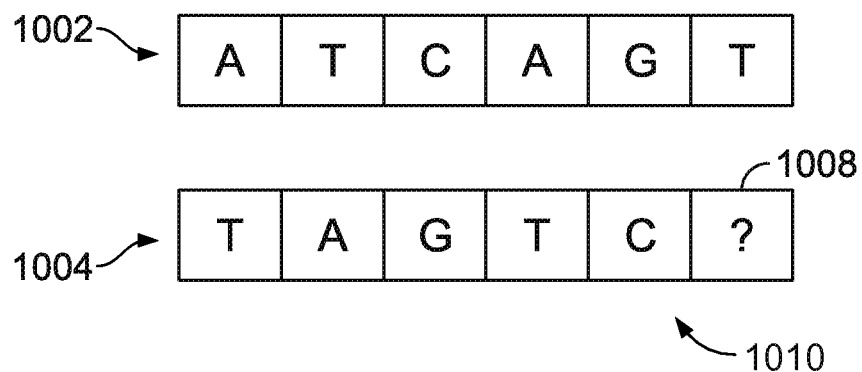
FIG. 10a is a diagram illustrating an embodiment of assaying an individual's DNA sequence with one sequence from a chip platform.
Figure 10B:
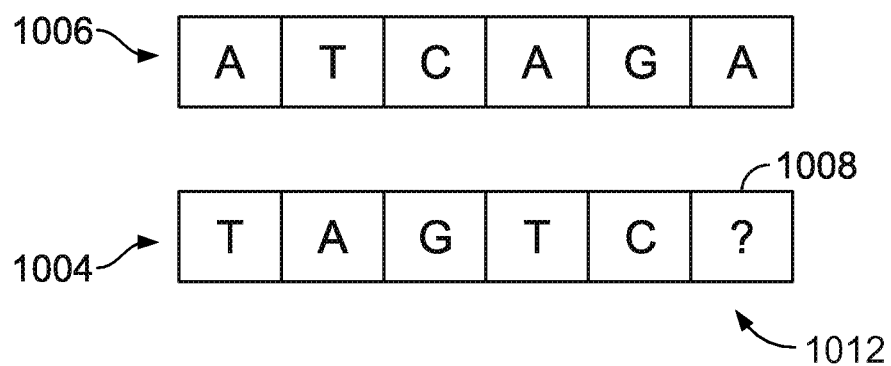
FIG. 10b is a diagram illustrating an embodiment of assaying an individual's DNA sequence with a second sequence from a chip platform.

FIGS. 10a-b illustrate an embodiment of assaying an individual's DNA sequence for one set of alleles with two different sequences from a chip platform. When individuals submit their DNA samples, there will be sequences that contain unknown SNPs, because SNPs are the sites on an individual's DNA which may vary from person to person. When an individual's DNA sequence is annealed to the known DNA sequences on the chip platform, the lab determines the intensity values by measuring how strong the bond is between the individual's sequence and the known sequence. FIG. 10a is a diagram illustrating an embodiment of assaying an individual's DNA sequence with one sequence from a chip platform. In FIG. 10a, a known sequence 1002 from the chip platform is assayed to the individual's DNA sequence 1004, which contains an unknown SNP at 1008 indicated with a "?" FIG. 10b is a diagram illustrating an embodiment of assaying an individual's DNA sequence with a second sequence from a chip platform. In FIG. 10b, another known sequence 1006 from the chip platform is assayed to the individual's DNA sequence 1004, which has the unknown SNP at 1008 indicated with "?" The length of the lines 1010 and 1012 around the DNA sequences provide a visual indication of the intensity values. As is illustrated, the intensity value in FIG. 10b is higher than the intensity value in FIG. 10a, indicating that the individual's unknown SNP is more likely A than T.

Figure 11:
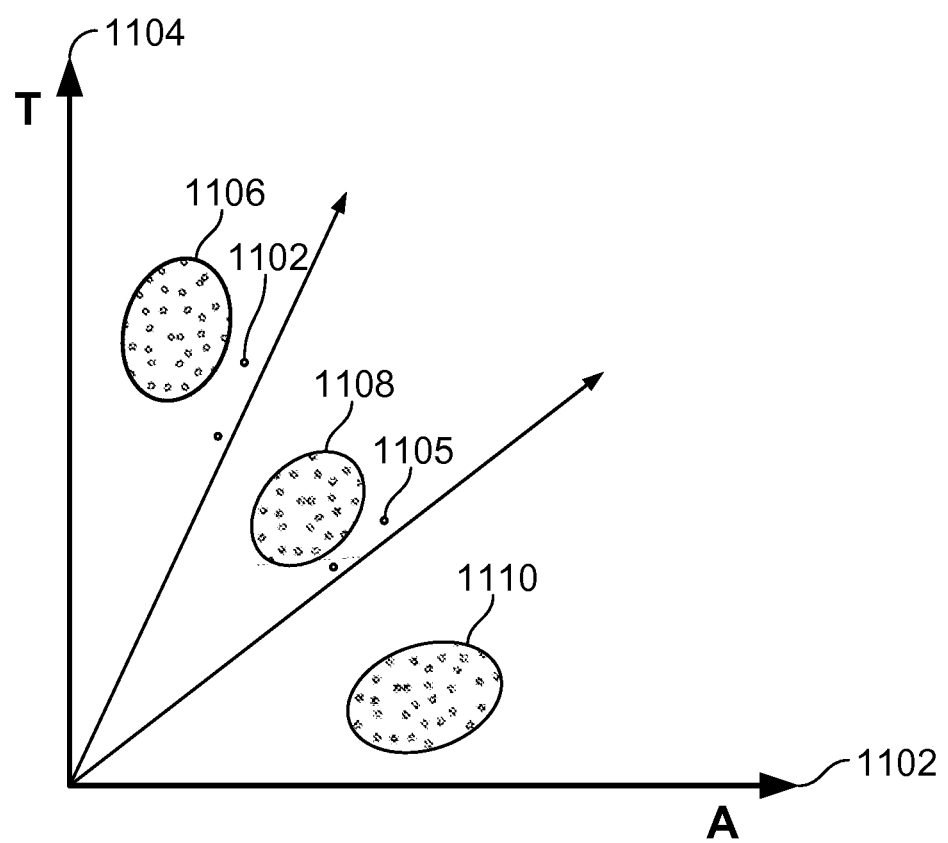
FIG. 11 is a graph illustrating an embodiment for making a call for a SNP given the two-dimensional vector for the values of a particular SNP.

The output of the genotyping process yields hybridization intensities for each allele in the form of a two-dimensional vector of "intensities." Genotypes are assigned, i.e. calls are made, based on comparing the relative strength of these intensities. To determine the appropriate bounds in two-dimensional space for calling each genotype in a given SNP for a given sample, a number of independent samples of other individuals' DNA are used and an assumption is made that the values of the SNP behave similarly across those independent samples. FIG. 11 is a graph illustrating an embodiment for making a call for a SNP given the two-dimensional vector for the values of a particular SNP. In the graph in FIG. 11, relative positions of a number of independent samples have been graphed. The x axis on the graph 1102 is assigned the value A. The y axis 1104 is assigned the value T. The dots on the graph indicate intensity values for the SNP from different individuals. 1106 indicates a cluster of plotted intensity values for the SNP for a number of individuals whose values have been graphed. Individuals whose two-dimensional vector of intensity values fall into that area have the value of TT. Therefore, if an individual's intensity value is plotted within the area of the cluster 1106, a call of TT may be made. 1108 is a cluster indicating the area for which a call of AT (or equivalently TA) may be made, and 1110 is a cluster indicating the area for which a call of AA may be made. An individual's intensity value, however, may fall outside these clusters and the result may be a "no-call" or NC in which the lab is unable to make a call for the SNP for the particular individual. 1102 and 1105 indicate intensity values which may result in a "no-call." There is, however, no rule or threshold that provides the appropriate bounds for distinguishing which intensity values will result in a "call" and which will result in a "no-call" that will work for all SNPs in two-dimensional space.

The above description of genotype calling relies on a specific implementation of sequencing-by-hybridization, and is a useful example upon which to base improvements. The output of all current sequencing methods is a signal (usually, fluorescence intensity) for the presence of each of the four bases at each position that can be substituted for the above-mentioned intensity. Since we apply a model that turns this intensity value into a probability, the following adjustments apply to either case.

Figure 12:
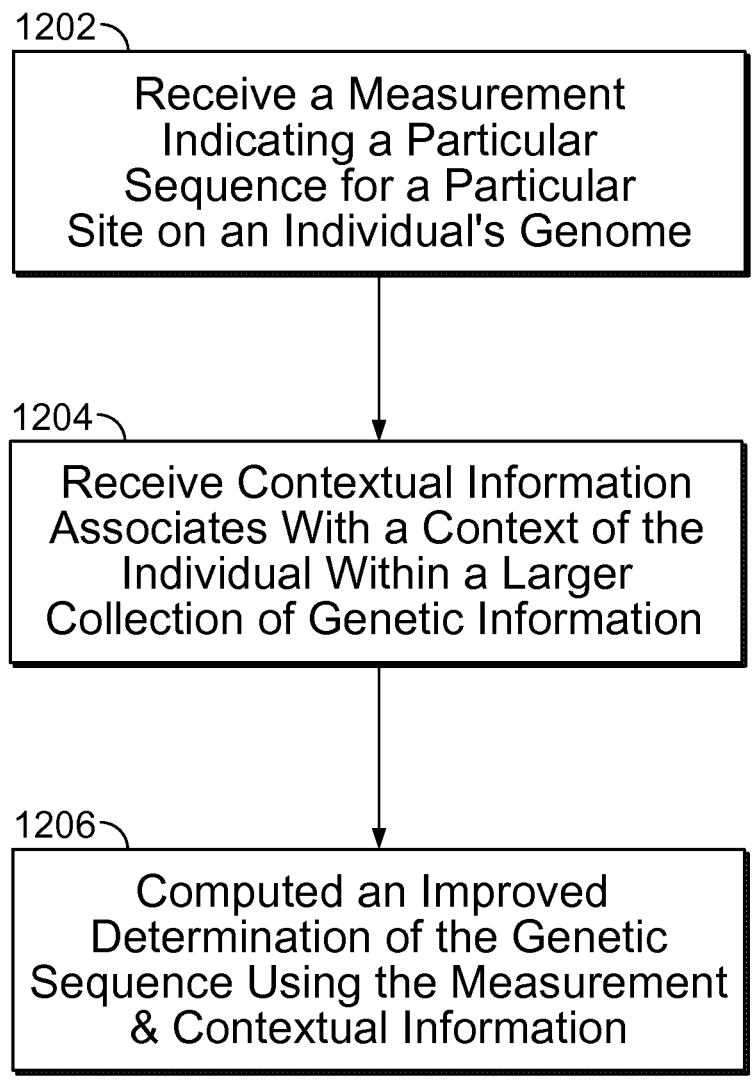
FIG. 12 is a flowchart illustrating an embodiment of a method for determining a genetic sequence for a particular site on an individual's genome.

It would be useful to include information in addition to the intensity data for calling genotypes. FIG. 12 is a flowchart illustrating an embodiment of a method for determining a genetic sequence for a particular site on an individual's genome. At step 1202, a measurement is received indicating a particular sequence for a particular site on an individual's genome. The measurement may comprise hybridization intensity values from the analysis of a lab which has received a sample of a particular individual's DNA.

At step 1204, contextual information associated with a context of the individual within a larger collection of genetic information may be received. Contextual information associated with a context of the individual within a larger collection of genetic information may comprise a variety of different types of information including: family information; population-specific information; linkage disequilibrium; and merging data from a number of probes. Using family inheritance, population-specific information, and linkage disequilibrium may be referred to as adjusting the prior because having this information about an individual allows for adjusting the prior probability of each genotype for a particular SNP on the individual based on the information.

Family Inheritance. The property of Mendelian inheritance predicts a level of consistency in genotypes between relatives. For example, if a mother has allele values for a particular SNP of AA and the father also has allele values for a particular SNP of AA, there is a probability of almost 100% that the child has allele values of AA for that particular SNP. We can refer to this information as the prior probability of an AA call for the child is 100%. If instead, the grandmother and grandfather each have allele values for the SNP of AA, the prior probability of an AA call for the child is less than 100%, but higher than it would be without this family information. Thus, if information about a particular individual's relatives' DNA is known, then this information can be used to help predict the calls for the individual's DNA sequence.

Population-specific Information. Because there is consistency in the genotypes of different ancestral groups, knowing that an individual is in a particular ancestral group provides contextual information for determining the value of a particular SNP for the individual. For example, if the probability that a particular SNP in Asians has an AA value is 90%, then the prior probability for AA for that SNP in an individual that is Asian is 90%.

Linkage Disequilibrium. With linkage disequilibrium, multiple SNPs can be used to provide information about another SNP. When an individual passes DNA to her child, the DNA sequences received from the individual's parents are split at certain points and recombined so that the individual passes virtually 50% of her DNA to the child. Sites on the genome where DNA splits in order to be recombined and passed on tend to be consistent. Therefore, there are certain regions of DNA that have tended to stay together for generations. This phenomenon is known as linkage disequilibrium. If two SNPs are close enough together, then a certain variant in one will indicate a certain variant in the other. Therefore, if a given SNP is in linkage disequilibrium with a nearby SNP, then information from either SNP can be used to provide information about the other SNP. For example, if the probability that a particular first SNP is AA given that a linked second SNP is GG is 90%, then the prior probability that the first SNP will be AA given that a call for the linked second SNP is GG is 90%. This information can be particularly helpful in determining a call for a SNP if the intensity values have resulted in a borderline no-call.

Merging Data from a Number of Probes. For a given SNP, the chip contains one or more probes that assay that SNP. The probes may be from the same platform, or different platforms (e.g. multiple types of SNP chip). The probes may be identical in sequence, or assay the SNP from both sides (i.e. upstream and downstream). The probe sequence may also be altered to account for nearby variation. For instance, one probe may be more appropriate for European individuals (assume Europeans have an A nucleotide at a certain position within the probe), and another probe more appropriate for African individuals (Africans have a G at the same position). The information from the different probes may be used as contextual information associated with a context of the individual within a larger collection of genetic information.

In some embodiments, the contextual information can be obtained from a database of individuals' DNA information, such as database 114.

If a SNP is being called based on multiple probes, the number of probes used may depend on the priority of the SNP. For example, for a SNP with a very high priority, there may be six probes used with three redundant probes assaying the SNP from each side.

Another example of using multiple probes is to use presence/absence probes in addition to normal probes. Using presence/absence probes may be helpful to determine the genotypes of DNA that is difficult to determine, for example, because of secondary structure in the probes, but is not limited to this use. Presence/absence probes are probes that overlap the SNP location. The presence of one variant of the SNP reduces the binding affinity of the probe, and so reduces the intensity for this probe. Generally, the overlap should occur within twenty nucleotides of the free end of the probe, in order for binding to be disrupted. As with normal SNP probes, some information is lost by using only intensity from one color channel instead of both color channels.

Multiple probes may also be used to account for polymorphisms within the genomic sequence complementary to the probe that can disrupt probe binding. Typically, the closer the polymorphism is to the free end of the probe, the greater the effect on binding.

If these polymorphisms are known (for example, they are cataloged in the database dbSNP), then it is possible to create multiple probes, complementary to each combination of these nearby variants. Genotype is then done using the appropriate probe, depending on the genotypes of the nearby polymorphisms. The number of probes used may depend on the priority of the SNP.

Multiple probes may also be used to account for multi-allelic SNPs, i.e. SNPs that can have more than two variants. In these cases, each allele needs to be assayed by at least one probe. Three for four alleles may be tested using two sets of probes. For example, on the Illumina platform, two pairs of Infinium I probes, or a pair of Infinium I probes and an Infinium II probe may be used.

At step 1206, the measurement associated with the particular sequence and the contextual information are used to compute an improved determination of the genetic sequence at the particular site on the individual's genome.

In various embodiments, any appropriate mapping and/or function (such as a majority vote) may be used to compute an improved determination of the genetic sequence at the particular site on the individual's genome. For example, a function can take as input the measurement and the contextual information and output a call or information used to make a call. For example, inputs to the function could include genotype intensity values, the individual's population assignment, and the known genotypes of the individual's parents; the function could be a logistic regression.

One embodiment for computing an improved determination of the genetic sequence using contextual information may include using statistical information, such as taking into account the measurement associated with the particular sequence and the contextual information and performing a statistical analysis using the measurement associated with the particular sequence and the contextual information to determine the call with the highest probability based on the measurement and the contextual information. One method is to use information derived from information about the individual to adjust the prior probability of a call received from a lab using hybridization. Other methods may be used. Below is a description of how statistical information may be used.

Statistical Information Related to Genotype Calling

To help assist in understanding the use of statistical information in genotyping calling the following examples and explanations are provided. In the illustrations provided below, the variables AA, AB and BB are used to illustrate the possible values for the two alleles making up a SNP. AA could represent AA, TT, CC or GG. AB could represent AT, TA, CG or CG. BB could represent any of the pairs AA, TT, CC or GG other than the pair represented by AA.

For a particular genotype, say AA, the following relationship is obtained from Bayes' Rule:

$$P(AA \mid D) = \frac{P(D \mid AA)P(AA)}{P(D)} \quad \text{(Equation 1)}$$

Where:

P(AA|D) is the posterior probability. The posterior probability is the probability that the genotype is AA (in this case) given that an intensity reading of D is obtained.

P(D|AA) is the observed probability. The observed probability is the probability of obtaining an intensity reading of D, given that the SNP is actually AA (in this case). The observed probability can be obtained using known data.

P(AA) is the prior probability.

P(D) is the probability of obtaining an intensity reading of D.

$$P(D)=P(D|AA)+P(D|AB)+P(D|BB) \quad \text{(Equation 2)}$$

The following is a specific example using some example numbers for the case in which there are three clusters defining three possible genotypes of a SNP—AA, AB, and BB:

Without prior information about the SNP, the prior probabilities are:

$P(AA)=0.33$ $P(AB)=0.33$ $P(BB)=0.33$

Given an intensity reading of D, the following observed probabilities can be observed (e.g., using known data):

P(D|AA)=0.01 (In other words, the probability of obtaining an intensity reading of D, given that the SNP is actually AA is 0.01)

P(D|AB)=0.1

P(D|BB)=0.01

If D is a point in the above figure, then D is relatively close to the AB cluster since there is a higher likelihood (0.1) of obtaining an intensity reading of D given that the SNP is AB.

The following can then be computed using Equation 1:

P(AA|D)P(D)=0.33×0.01=0.0033

P(AB|D)P(D)=0.33×0.1=0.033

P(BB|D)P(D)=0.33×0.01=0.0033

From Equation 2, P(D)=0.01+0.1+0.01=0.12
Therefore, the posterior probabilities are:

P(AA|D)=0.0033/0.12=0.0275

P(AB|D)=0.033/0.12=0.275

P(BB|D)=0.0033/0.12=0.0275

In some embodiments, a call is made based on which of the posterior probabilities is the greatest. In this case, P(AB|D) is the greatest, so the call made is AB.

The additional computation of dividing by P(D) isn't necessary if the call is made based on which of the posterior probabilities is greatest. However, in some embodiments, the call is made based on other factors, so it may be necessary in some embodiments to divide by P(D).

In the above example, if there is no prior information about the SNP, the prior probability of each call is uniform over AA, AB, and BB. In other words, before obtaining the intensity data, the expectation is that an individual will have an equal chance of 0.33 of being AA, AB, or BB. In various embodiments, the prior probability of each genotype can be adjusted based on contextual information associated with a context of the individual within a larger collection of genetic information. For example, the contextual information could include family information, population-specific information, and/or linkage disequilibrium as discussed above.

As discussed above, one embodiment of contextual information may include information about an individual's family member's DNA. When information about an individual's family members' DNA has been collected, for example in a database, making calls regarding that individual's DNA may be improved by using the information about her family member's DNA. Specifically, we exploit the property of Mendelian inheritance which predicts a level of consistency in genotypes between relatives. For instance, if a mother and father's calls at rs123 are AA and AA, respectively, then we know that the probability that their child will be AA is close to 100%, allowing for the probability of miscalls in each parent's data, and the probability of a novel mutation event. This is the prior probability of an AA call for the child, before seeing the SNP intensity data. Applying this example to the above equations, the prior probabilities could be adjusted to:

P(AA)=0.99

P(AB)=0.005

P(BB)=0.005

This would cause the posterior probabilities to be:

P(AA|D)=0.00825

P(AB|D)=0.00417

P(BB|D)=0.00042

In embodiments in which a call is made based on which of the posterior probabilities is the greatest, the call made would then be AA since P(AA|D) is the greatest. As illustrated by this example, adjusting the prior probability can change the final call—in this case, from AB to AA.

In another embodiment, contextual information may include population-specific information. First, the individual is assigned to an ancestral group (in the simplest case, European, Asian or African). If the individual is admixed (i.e. a mixture of two ancestral groups), then it may be necessary to assign each SNP to an ancestral group. Then the genotype frequency from the appropriate population can be used as a prior probability. For instance, if the probability that rs123 is AA in Asians is 90%, then the prior probability that a genotypically Asian individual (i.e. an individual with a genotype that significantly more often contains SNP variants that are common among Asians than other ancestral groups) is AA in rs123 is also 90%.

In another embodiment, contextual information may include information from linkage disequilibrium. Certain regions of DNA tend to stay together when passed from parent to child, known as linkage disequilibrium. If a given SNP is in linkage disequilibrium with a nearby SNP, then information from either SNP can be used to provide information about the other SNP. For instance, if the probability that a SNP, rs123, is AA given that a linked SNP, rs456, is GG is estimated at 90% (P(rs123=AA|rs456=GG)=0.9), then the prior probability that rs123 will be AA given a call for rs456 can be calculated accordingly. For example:

Assuming a nearby SNP, rs456 is GG, and we have LD information on whether our SNP is AA, AG or GG based on this. The new prior probabilities are now:

P(AA|rs456=GG)=0.9

P(AG|rs456=GG)=0.05

P(GG|rs456=GG)=0.05

Then the posterior is:

P(AA|D)=0.075

P(AG|D)=0.042

P(GG|D)=0.0042

This is typically helpful if one of the two SNPs in LD is a borderline no-call (i.e. has probe intensities that do not enable a high confidence call), and the linked SNP is highly likely to be a particular genotype. LD is highly dependent on ancestry, so the ancestry of the individual can also be taken into account. Linkage disequilibrium has been estimated for each of the Hapmap populations (European, Asian and African) and can be estimated using a database of individuals' genetic information, such as database 114.

In another embodiment the contextual information may include information from multiple probes. For a given SNP, the chip contains one or more probes that assay that SNP. The probes may be from the same platform, or different platforms (e.g. multiple types of SNP chip). The probes may be identical in sequence, or assay the SNP from both sides (i.e. upstream and downstream). The probe sequence may also be altered to account for nearby variation. For instance, one probe may be more appropriate for European individuals (assume Europeans have an A nucleotide at a certain position within the probe), and another probe more appropriate for African individuals (Africans have a G at the same position).

One embodiment involving multiple probes is to average the intensities of all the probes for a particular SNP. Another embodiment is to estimate a likelihood (observed probability) for each of the calls for each probe independently using the standard intensity-based calling methods and combine the resulting likelihoods. If it assumed that the likelihoods are independent, the likelihoods can be multiplied.

Another embodiment involves using "non-standard" probes. The chip may contain "non-standard" probes in which the probes assay for a SNP variant in an atypical manner. For instance, we can create a probe that overlaps a true SNP, with the probe assaying an unchanging position near the SNP. The probe could then be used to differentiate between two SNP variants because only one variant would result in the probe binding and emitting light; the non probe-binding variant would appear dark. Hence, the probe acts as a presence/absence test (the same approach that would be used for detecting deletions), and uses only one of the two available color channels. In order to integrate this type of data, we require a different model for the expected clustering pattern, but the likelihoods can still justifiably be combined. Here, the clustering pattern is simply three levels of intensity on one dimension, corresponding to one of: two probe-binding variants absent, one probe-binding variant present and one absent, two probe-binding variants present.

In various embodiments, the observed probability of each genotype can be adjusted based on contextual information associated with a context of the individual within a larger collection of genetic information. For example, the contextual information could include information associated with merging data from a number of probes.

For example, in the above example, adjusting the observed probabilities would comprise adjusting: P(D|AA), P(D|AB), and P(D|BB). Adjusting these values would then cause the posterior probabilities to change in value.

As an example, if there are three probes per chip, there would be three observed probabilities per genotype, one for each probe: $P_{probe1}(D|AA)$, $P_{probe2}(D|AA)$, and $P_{probe3}(D|AA)$. P(D|AA) in Equations 1 and 2 can then be computed as follows:

$$P(D|AA) = P_{probe1}(D|AA) \times P_{probe2}(D|AA) \times P_{probe3}(D|AA)$$

In various embodiments, more than one type of contextual information may be used to improve the call. For example, a combination of two or more of family information, population-specific information, and linkage disequilibrium may be used. If there is a conflict, say between family information and linkage disequilibrium, one of the types of contextual information may be prioritized over the other, depending on which source of evidence is more probable. For example, family information could trump linkage disequilibrium.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system for processing genetic data, including:
a processor configured to:
receive two or more genetic data sets for an individual from one or more genetic data sources, wherein the genetic data sets comprises information pertaining to the individual's deoxyribonucleic acid (DNA) data;
merge the genetic data sets from the one or more genetic data sources to obtain a set of merged genetic data for the individual, including to:
identify a single nucleotide polymorphism (SNP) that is a duplicate SNP of the genetic data sets, wherein the SNP is associated with a variation that occurs at a location in the individual's DNA sequence, and values corresponding to the duplicate SNP in the genetic data sets are different;
analyze the values of the duplicate SNP to resolve a discrepancy attributed to different values corresponding to the duplicate SNP and automatically determine an appropriate value that corresponds to the duplicate SNP, the analysis and determination being based at least in part on contextual information; and
store the set of merged genetic data for the individual; wherein
the appropriate value that is determined is stored in the set of merged genetic data, and a different value that corresponds to the duplicate SNP is not stored in the set of merged genetic data; and
a memory coupled to the processor and configured to provide the processor with instructions.

2. The system of claim 1, wherein to store the set of merged genetic data includes to create a data structure for the individual's data.

3. The system of claim 2, wherein the data structure includes information relevant to a specific application.

4. The system of claim 2, wherein to store the set of merged genetic data includes to store the data structure in a database that can be accessed by an application for analyzing DNA data.

5. The system of claim 4, wherein the application for analyzing DNA data includes a website.

6. The system of claim 1, wherein to receive two or more genetic data sets for an individual includes to create a data structure for each genetic data set and store the data for each genetic data set in a data structure.

7. The system of claim 1, wherein to merge the genetic data sets from the one or more genetic data sources includes to create a first data structure for storing the individual's merged genetic data; and a second data structure for storing a more limited set of the individual's data.

8. The system of claim 1, wherein to store the set of merged genetic data for the individual includes to store the data in a particular order or location that is the same for every individual.

9. The system of claim 1, wherein the two or more data sets include an intensity value, a genotype call, or a confidence value associated with a genotype call.

10. The system of claim 1, wherein the set of merged data is stored in a structure having a plurality of entries each corresponding to a SNP.

11. The system of claim 1, wherein the contextual information includes linkage disequilibrium information.

12. The system of claim 1, wherein the genetic data source includes a genotyping chip or platform.

13. The system of claim 1, wherein the contextual information includes family inheritance information.

14. The system of claim 1, wherein the contextual information includes population-specific information.

15. The system of claim 11, wherein a lookup table is provided for mapping each of the plurality of entries to a chromosome positional index.

16. The system of claim 1, wherein the contextual information includes information pertaining to the SNP that was assayed by multiple probes.

17. The system of claim 1 wherein duplicate SNP to select a value to be stored for the duplicate SNP comprises adjusting a prior probability.

18. The system of claim 1 wherein duplicate SNP to select a value to be stored for the duplicate SNP comprises adjusting an observed probability.

19. A method for processing genetic data, including:
receiving two or more genetic data sets for an individual from one or more genetic data sources, wherein the genetic data sets comprises information pertaining to the individual's deoxyribonucleic acid (DNA) data;
merging the genetic data sets from the one or more genetic data sources to obtain a set of merged genetic data for the individual, including:
identifying a single nucleotide polymorphism (SNP) that is a duplicate SNP of the genetic data sets, wherein the SNP is associated with a variation that occurs at a location in the individual's DNA sequence, and values corresponding to the duplicate SNP in the genetic data sets are different;
analyzing the values of the duplicate SNP to resolve a discrepancy attributed to different values corresponding to the duplicate SNP and automatically determining an appropriate value that corresponds to the duplicate SNP, the analysis and determination being based at least in part on contextual information; and
storing the set of merged genetic data for the individual; wherein
the appropriate value that is determined is stored in the set of merged genetic data, and a different value that corresponds to the duplicate SNP is not stored in the set of merged genetic data.

20. A computer program product for processing genetic data, the computer program product being embodied in a computer readable medium and comprising computer instructions for:
receiving two or more genetic data sets for an individual from one or more genetic data sources, wherein the genetic data sets comprises information pertaining to the individual's deoxyribonucleic acid (DNA) data;
merging the genetic data sets from the one or more genetic data sources to obtain a set of merged genetic data for the individual, including:
identifying a single nucleotide polymorphism (SNP) that is a duplicate SNP of the genetic data sets, wherein the SNP is associated with a variation that occurs at a location in the individual's DNA sequence, and values corresponding to the duplicate SNP in the genetic data sets are different;
analyzing the values of the duplicate SNP to resolve a discrepancy attributed to different values corresponding to the duplicate SNP and automatically determining an appropriate value that corresponds to the duplicate SNP, the analysis and determination being based at least in part on contextual information; and
storing the set of merged genetic data for the individual; wherein
the appropriate value that is determined is stored in the set of merged genetic data, and a different value that corresponds to the duplicate SNP is not stored in the set of merged genetic data.

* * * * *

UNITED STATES PATENT AND TRADEMARK OFFICE
CERTIFICATE OF CORRECTION

PATENT NO. : 8,645,343 B2
APPLICATION NO. : 12/583842
DATED : February 4, 2014
INVENTOR(S) : Alexander Wong et al.

Page 1 of 1

It is certified that error appears in the above-identified patent and that said Letters Patent is hereby corrected as shown below:

In the claims

In Claim 17, at column 17, line 4, change "wherein duplicate SNP" to --wherein analyzing the values of the duplicate SNP--

In Claim 18, at column 17, line 7, change "wherein duplicate SNP" to --wherein analyzing the values of the duplicate SNP--

Signed and Sealed this
Nineteenth Day of July, 2016

Michelle K. Lee
*Director of the United States Patent and Trademark Office*